US011154420B2

(12) United States Patent
Yamamoto et al.

(10) Patent No.: US 11,154,420 B2
(45) Date of Patent: Oct. 26, 2021

(54) OPHTHALMIC INJECTION DEVICE

(71) Applicant: Oxular Limited, Oxford (GB)

(72) Inventors: Ronald K. Yamamoto, San Francisco, CA (US); Stanley R. Conston, San Carlos, CA (US); Robert Steven Bley, Menlo Park, CA (US)

(73) Assignee: Oxular Limited, Oxford (GB)

(*) Notice: Subject to any disclaimer, the term of this patent is extended or adjusted under 35 U.S.C. 154(b) by 502 days.

(21) Appl. No.: 15/760,717

(22) PCT Filed: Sep. 16, 2016

(86) PCT No.: PCT/EP2016/072024
§ 371 (c)(1),
(2) Date: Mar. 16, 2018

(87) PCT Pub. No.: WO2017/046358
PCT Pub. Date: Mar. 23, 2017

(65) Prior Publication Data
US 2018/0256393 A1 Sep. 13, 2018

Related U.S. Application Data
(60) Provisional application No. 62/220,165, filed on Sep. 17, 2015.

(51) Int. Cl.
*A61M 5/168* (2006.01)
*A61F 9/00* (2006.01)
(Continued)

(52) U.S. Cl.
CPC ......... *A61F 9/0017* (2013.01); *A61M 5/1452* (2013.01); *A61M 5/16881* (2013.01);
(Continued)

(58) Field of Classification Search
CPC ........ A61F 9/00; A61F 9/0017; A61F 9/0008; A61F 9/007; A61F 9/00736;
(Continued)

(56) References Cited

U.S. PATENT DOCUMENTS 1,641,976 A * 9/1927 Laurent ................. A61M 5/204
604/184
3,890,971 A 6/1975 Leeson
(Continued)

FOREIGN PATENT DOCUMENTS

CN 103327939 9/2013
DE 102010048085 4/2012
(Continued)

OTHER PUBLICATIONS

Final Office Action dated Oct. 28, 2019 in related U.S. Appl. No. 15/512,130.
(Continued)

*Primary Examiner* — Jason E Flick
(74) *Attorney, Agent, or Firm* — Stradley Ronon Stevens & Young, LLP

(57) ABSTRACT

A device for controlled delivery of an injection material to tissue spaces of an eye that are not normally open, such as the subconjunctival space, the suprachoroidal space and the subretinal space. The device comprises an elongated body with a hollow cannula at the distal end, a slidable plunger at the proximal end, and a reservoir for the material to be injected residing between the cannula and the plunger. The plunger is mechanically coupled to a source of force such as a spring or pressurized gas reservoir such that an injection force is applied to the injection material within the device prior to delivery of the injection material into an eye. A valve that is normally closed to prevent flow of the injection material during application of the injection force is placed in (Continued)

the flow path between the cannula and reservoir. Due to the injection force placed on the injection material, actuation of the valve allows controlled flow from the reservoir through the cannula and into the tissue space.

26 Claims, 8 Drawing Sheets

(51) Int. Cl.
| | | |
|---|---|---|
| *A61M 5/20* | (2006.01) | |
| *A61M 5/145* | (2006.01) | |
| *A61M 5/315* | (2006.01) | |
| *A61M 5/32* | (2006.01) | |
| *A61M 5/31* | (2006.01) | |

(52) U.S. Cl.
CPC ........... *A61M 5/2053* (2013.01); *A61M 5/315* (2013.01); *A61M 5/329* (2013.01); *A61M 2005/3128* (2013.01); *A61M 2205/8218* (2013.01); *A61M 2210/0612* (2013.01)

(58) Field of Classification Search
CPC .. A61M 2005/3128; A61M 2205/8218; A61M 2210/0612; A61M 5/1452; A61M 5/16881; A61M 5/2053; A61M 5/315; A61M 5/329; A61M 5/178; A61M 5/31; A61M 5/20; A61M 5/142; A61M 5/145; A61M 5/168
See application file for complete search history.

(56) References Cited

U.S. PATENT DOCUMENTS

| | | | |
|---|---|---|---|
| 5,236,424 | A | 8/1993 | Imran |
| 5,250,031 | A | 10/1993 | Kaplan |
| 5,295,972 | A | 3/1994 | Mischenko |
| 5,358,489 | A | 10/1994 | Wyrick |
| 5,665,071 | A | 9/1997 | Wyrick |
| 5,957,897 | A | 9/1999 | Jeffrey |
| 6,409,706 | B1 | 6/2002 | Loy |
| 2003/0057347 | A1 | 3/2003 | Weiss |
| 2004/0039337 | A1 | 2/2004 | Letzing |
| 2004/0078006 | A1 | 4/2004 | Bills |
| 2005/0070848 | A1 | 3/2005 | Kim |
| 2006/0141049 | A1 | 6/2006 | Lyons et al. |
| 2007/0202186 | A1 | 8/2007 | Yamamoto et al. |
| 2008/0234637 | A1 | 9/2008 | McConnell et al. |
| 2009/0036827 | A1 | 2/2009 | Cazzini |
| 2009/0148527 | A1 | 6/2009 | Robinson et al. |
| 2010/0104654 | A1* | 4/2010 | Robinson ............. A61K 9/1647 424/501 |
| 2010/0249721 | A1 | 9/2010 | Guillermo |
| 2011/0238075 | A1 | 9/2011 | Luke et al. |
| 2012/0271272 | A1* | 10/2012 | Hammack ........... A61F 9/00727 604/500 |
| 2013/0096534 | A1 | 4/2013 | Orilla et al. |
| 2013/0202186 | A1 | 8/2013 | Yamamoto et al. |
| 2013/0296825 | A1 | 11/2013 | Lerner |
| 2013/0345618 | A1* | 12/2013 | Auld ................... A61M 5/3156 604/24 |
| 2015/0223977 | A1 | 8/2015 | Oberkircher et al. |
| 2015/0351958 | A1 | 12/2015 | Contiliano et al. |
| 2017/0224534 | A1 | 8/2017 | Andino et al. |

FOREIGN PATENT DOCUMENTS

| | | |
|---|---|---|
| EP | 1450884 | 9/2004 |
| EP | 2248494 | 11/2010 |
| GB | 2531910 | 5/2016 |
| GB | 2536517 | 9/2016 |
| JP | H10-507239 | 8/1996 |
| JP | H8-507239 | 8/1998 |
| WO | 2004/094823 | 11/2004 |
| WO | 2006044029 | 4/2006 |
| WO | 2007100745 | 11/2007 |
| WO | 2009089409 | 7/2009 |
| WO | 2010003011 | 1/2010 |
| WO | WO2010147661 | 12/2010 |
| WO | 2011117592 | 9/2011 |
| WO | 2012051575 | 4/2012 |
| WO | 2012059449 | 5/2012 |
| WO | 2012115911 | 8/2012 |
| WO | WO2013028936 | 2/2013 |
| WO | 2013151904 | 10/2013 |
| WO | 2013/188595 | 12/2013 |
| WO | 2016/042162 | 3/2016 |
| WO | 2016040635 | 3/2016 |
| WO | 2016042162 | 3/2016 |
| WO | 2016042163 | 3/2016 |

OTHER PUBLICATIONS

Office Action dated Apr. 8, 2019 received in related U.S. Appl. No. 15/512,130.
Einmabl et al., "Evaluation of a Novel Biomaterial in the Suprachoroidal Space of the Rabbit Eye", IOVS, 2002, 43(5), pp. 1533-1539.
Non-Final Office Action dated Nov. 27, 2020 in related U.S. Appl. No. 15/512,130.
Notice of Allowance dated Apr. 26, 2021 in related U.S. Appl. No. 15/512,130.

* cited by examiner

OPHTHALMIC INJECTION DEVICE

RELATED APPLICATIONS

This application is a 35 U.S.C. § 371 national phase application of PCT Application No. PCT/EP2016/072024, filed Sep. 16, 2016, which claims priority to U.S. Provisional Application 62/220,165, filed Sep. 17, 2015. Any and all applications for which a foreign or domestic priority claim is identified in the Application Data Sheet as filed with the present application are hereby incorporated by reference under 37 CFR 1.57. Where allowable all patents and patent applications referred to herein are hereby incorporated by reference in their entirety.

BACKGROUND OF INVENTION

Due to the unique anatomy and physiology of the eye, multiple barriers exist that prevent significant transport of drugs to ocular tissues. The blood vessels of the eye have restricted permeability due to the blood-ocular barriers that regulate intraocular fluid. Due to these blood-ocular barriers, systemically administered drugs do not reach significant concentration in ocular tissues. Some drugs may be delivered to the front, anterior portion of the eye by drops but reaching significant therapeutic concentrations in the posterior portion of the eye and the retina is generally not achieved with topical methods of administration.

Due to the ocular barriers for drug transport in the eye and the need for treating the retina in the posterior portion of the eye, many ocular therapeutics are administered by injection. In the treatment of certain diseases and tissues of the eye, it is often desired to inject a therapeutic agent to a specific tissue layer to create a space that is not normally present. One example is the subconjunctival space where injection of a fluid creates a space or bleb between the conjunctiva and sclera. The pressure and flow properties of the administered fluid create a space for the injection material that acts as a depot for the therapeutic agent.

Due to recent advances in treating the retina with specific gene and cell therapies, a therapeutic agent is often desired to be injected in the subretinal space with a very small gauge cannula where the injection of a fluid creates a bleb between the retina and retinal pigmented epithelium or between the retina and choroid. However for subretinal injections, the injection must be performed in a manner to prevent trauma to the sensitive retinal tissues or formation of a bleb that may result in undesired permanent detachment of the retina.

SUMMARY OF THE INVENTION

In keeping with the foregoing discussion, the present invention provides an ophthalmic injector for injection that provides highly controlled delivery of a therapeutic agent in a fluid through a small gauge cannula. The small gauge of the cannula provides self-sealing properties to the injection site to prevent leakage of the injected material during delivery and after removal of the cannula. The small gauge cannula is also desired to minimize trauma to sensitive ocular tissues.

The device comprises an elongated body having a hollow cannula at the distal end. A reservoir holds the injection material to be delivered through the cannula. A plunger within the elongated body of the device is acted on by a force element, such as a compression spring or gas reservoir, that provides an injection force to the injection material. The device also comprises a valve mechanism between the cannula and the reservoir that allows actuation of injection and progressive control of the injection rate. The injection material in the reservoir is placed under pressure by the force element prior to placement of the cannula into the target tissue or tissue space for injection. The mechanism allows actuation of the valve by the user to perform and regulate the injection rate without manipulation of a plunger as with a syringe, allowing controlled one-handed injection of the injection material into tissues or tissue spaces. The high degree of control of the tissue placement of the device while also controlling the injection rate allows greater precision and ease when injecting into tissues spaces that are not normally open, such as the subconjunctival space, the supraciliary space, the suprachoroidal space, the subtenon space and the subretinal space.

In one embodiment of the device, the device also comprises a tissue interface on the distal tip. The tissue interface is slidably disposed on the outer diameter of the cannula such that the tissue interface makes contact with the surface of the target tissue for injection and remains on the surface during advancement of the cannula into the tissues and delivery of the injection material. The tissue interface serves to stabilize the tissue surface especially for sensitive tissues such as the retina and may also provide a seal to limit leakage during delivery of the injection material.

These and other aspects of the invention will be made apparent from consideration of the following detailed description in conjunction with the accompanying drawing figures.

Some embodiments provide an injection device comprising an elongated body with a hollow cannula secured to the distal end of the body, a reservoir for an injection material to be delivered through the cannula, a plunger with a force element that is configured to provide an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, and wherein progressive actuation of the valve actuation mechanism increases the flow rate of injection.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, wherein the valve comprises a flow path comprising an elastically deformable material or combination of materials and a mechanism external to the flow path that applies a compression force to close the flow path in the valve, and wherein relieving of the compression force by the valve actuation mechanism allows the elastic return of the flow path from a closed or partially closed configuration to a configuration with a decreased flow resistance. Suitably, the elastically deformable material or combination of materials may comprise an elastomeric tube.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, wherein the valve comprises a flow path comprising an elastically deformable material or combination of materials and a mechanism external to the flow path that applies a compression force to close the flow path in the valve, wherein the mechanism comprises two opposing surfaces coupled to a spring force acting to reduce the distance between the two surfaces, wherein the two opposing surfaces are configured on opposite sides of the flow path to compress and increase the flow resistance of the flow path.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, wherein the valve comprises an internal valve spring, a sealing element and a valve seat, wherein the sealing element is pressed against the valve seat under a sealing force by the valve spring, and an external force against the valve by the valve actuation mechanism deforms the valve seat to create a flow path.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, wherein the valve comprises an internal valve spring, a sealing element and a valve seat, wherein the sealing element is pressed against the valve seat under a sealing force by the valve spring, and at least one of the sealing element and the valve seat are magnetic or paramagnetic, wherein the valve actuation mechanism comprises a magnet which when translated opens a flow path between the sealing element and the valve seat.

Some embodiments provide an injection device comprising an elongated body with a hollow cannula secured to the distal end of the body, a reservoir for an injection material to be delivered through the cannula, a connector, valve or septum to fill the reservoir, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, and wherein progressive actuation of the valve actuation mechanism increases the flow rate of injection.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, and wherein progressive actuation of the valve actuation mechanism increases the flow rate of injection, and wherein the reservoir comprises a cartridge that is inserted into the device prior to use.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, and wherein progressive actuation of the valve actuation mechanism increases the flow rate of injection.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, and wherein progressive actuation of the valve actuation mechanism increases the flow rate of injection, wherein the valve actuation mechanism comprises two opposing mechanical elements on opposite sides of the body of the device configured to be activated by squeezing of the elements toward each other.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, wherein the force element is coupled to a damping mechanism.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, wherein the device additionally comprises a tissue interface secured to the distal end of the cannula.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, wherein the device additionally comprises a tissue interface secured to the distal end of the cannula, wherein the tissue interface is elastically compressible in length.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, wherein the device additionally comprises a tissue interface secured to the distal end of the cannula and a collapsible element between the body of the device and the tissue interface.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, and a method for treatment of an eye comprising, providing an injection force to the injection material, placing the distal tip of the cannula of the injection device into the subretinal space of an eye, and activating the actuation mechanism to deliver the injection material to the subretinal space.

Some embodiments provide an injection device comprising an elongated body with a hollow cannula secured to the distal end of the body, a reservoir for an injection material to be delivered through the cannula, a plunger with a force element that provides an injection force to the injection material, a valve disposed in the flow path between the reservoir and the cannula wherein the valve is normally closed with the injection force applied to the injection material, and a valve actuation mechanism for the valve that is external to the valve, wherein the valve actuation mechanism is attached to the elongated body, wherein actuation of the valve actuation mechanism opens a flow path through the valve, wherein progressive actuation of the valve actuation mechanism increases the flow rate of injection, and a method for treatment of an eye comprising providing an injection force to the injection material, placing the distal tip of the cannula of the injection device into the subconjunctival space of an eye; and activating the actuation mechanism to deliver the injection material to the subconjunctival space.

Preferred aspects of the second and subsequent aspects of the invention are as for the first aspect mutatis mutandis.

DESCRIPTION OF THE INVENTION

Figure 1:
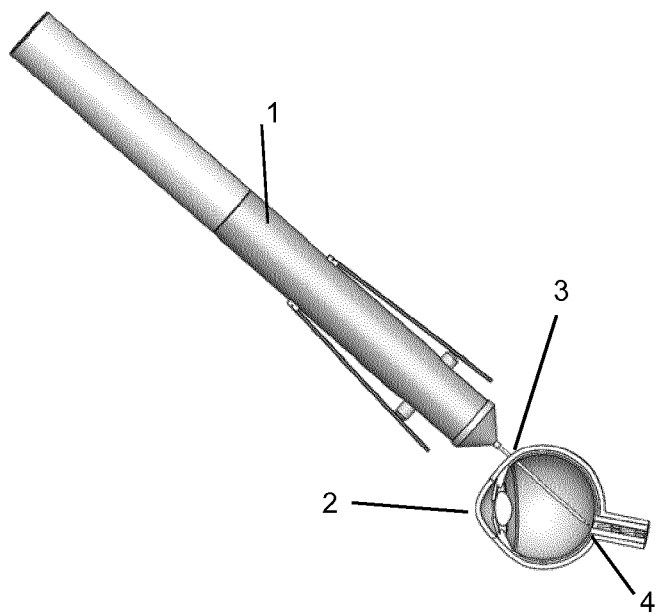
FIG. 1 depicts the device applied to an eye.

The invention is an ophthalmic injector for the delivery of therapeutic agents in a fluid medium through a small gauge cannula to tissues or tissue spaces of the eye. The device comprises an elongated body with a hollow cannula at the distal end, a slidable plunger at the proximal end, and a reservoir for the material to be injected residing between the cannula and the plunger. When a low volume of material is to be injected, the lumen of the cannula may also serve as the reservoir or a portion of the reservoir. The plunger acts to push the injection material from the reservoir, into the cannula and through the cannula to the desired tissue location. The plunger is mechanically coupled to a source of force such as a spring or pressurized gas reservoir such that an injection force is applied to the injection material within the device after the injection material is placed in the reservoir and prior to injection of the injection material into an eye. A valve is placed in the flow path between the cannula and reservoir. The valve is normally closed to prevent flow of the injection material during application of the injection force. The injection force may be applied to the injection material prior to the placement of the distal tip of the injection device into the desired tissue location for injection. Due to the injection force placed on the injection material, actuation of the valve allows flow from the reservoir to the cannula and into tissues or tissue spaces. Progressive actuation of the valve progressively increases the flow through the valve, providing flow regulation.

In one embodiment, the force element is self-contained in the device or is integrated on the body of the device. The injection material is placed into the reservoir portion of the body, in a manner similar to a syringe, through a connector, valve or septum in fluid connection to the reservoir. Alternatively, the injection material may be in a cartridge which is placed in the reservoir region of the device. Placement of the injection material in the device preloads a force element such as a compression spring acting on the plunger providing an injection force on the injection material in the reservoir. Other mechanisms may be provided for activating the injection force. For example, the injection force may be activated by a mechanism to compress the force element from the exterior of the device. In another option, the injection force may be activated by mechanically releasing a constrained force element or gas prior to use. In one embodiment a Luer fitting or other connector is provided for filling the reservoir with the injection material and a one-way valve prevents backflow of the injection material through the connector.

The device allows precise control of the position of the cannula by the user. The cannula is secured to the body to the device to allow direct control of the distal tip of the cannula when the body of the device is held. Since the injection force is provided by the force element, the plunger of the device does not have to be pushed distally by the hand holding the device or with another hand, allowing the device to be held and used in a natural, highly controllable position as with a writing instrument or scalpel. Further aiding the positional control of the device is a valve actuation mechanism such as a push button, lever or slide mechanism that can be moved by the index finger and/or thumb while holding and adjusting the position of the device for injection into tissue. The actuation mechanism is located in or on the distal portion of the body of the device to allow use in the hand position used to position the device in the target tissue. The actuation mechanism allows control of the flow regulating valve while simultaneously positioning the distal tip of the device in the eye.

Certain valve designs are advantageous for the injection device. The valve is designed to not only initiate flow but to also allow regulation of the flow rate depending on the degree of valve actuation. The valve is designed to allow use with an actuation mechanism that is secured to the body of the device or integrated into the body of the device. The portion of the actuation mechanism to be activated by the user is located on an external surface of the device in a location to be used while holding the injection device in a comfortable position as with a writing instrument or scalpel. The actuation mechanism of the injection device is preferably external to the valve, meaning that no element of the actuation mechanism is within the valve, in the flow pathway or in contact with the injection material. The external valve mechanism of the injection device allows fine control of flow rate while having no potential flow path between the valve and the surfaces or spaces external to the valve. A valve mechanism with a potential flow path between the valve and the surfaces or spaces external to the valve provides a path for leakage and contamination of the sterile injection material. Such valve designs require seals and present a source of failure. The valve mechanisms may be designed so as to limit the dead volume of the injectate within the valve.

In one embodiment, the injection device comprises a valve residing between the cannula and reservoir that is actuated by deforming the valve externally. The valve is normally closed by the action of an internal valve spring or compression element to press a sealing element against a valve seat. The valve seat is formed of a deformable material such as a rubber or soft polymer where a force on the external surface of the valve compresses the valve to distort the shape of the seat to create a flow path. The size of the flow path is proportional to the force on the external surface, allowing the flow rate to be controlled by the amount of force applied. The sealing element may be spherically shaped or conically shaped to press into the valve seat with complementary size and geometry to form a seal. Application of a force on the valve near the valve seat opens one or more flow paths in the valve seat to allow for delivery of the injection material. Progressive application of the force progressively opens the flow path in the valve seat to increase flow through the valve.

In one embodiment, the injection device comprises a valve residing between the cannula and reservoir that is actuated by relieving a closing force acting on the valve. The valve is normally closed by the action of a mechanism external to the valve that applies a compression force to close the flow path in the valve. The portion of the flow path that is responsive to the external closing force is formed of an elastically deformable material or combination of materials. The relief of the external closing force on the valve is proportional to the force applied to an external actuation mechanism to allow the flow path to open and decrease the flow resistance of the valve. The resultant decrease in flow resistance by opening of the flow path is in proportion to the force applied to the actuation mechanism to provide flow control. Progressive application of force to the actuation mechanism results in progressive opening of the flow path to increase flow through the valve. In one embodiment the flow path comprises a segment of elastic tubing. In one embodiment the mechanism that applies a compression force to close the flow path comprises two opposing surfaces coupled to a spring force acting to compress the segment of flow path between the two surfaces. The two surfaces are located on opposite sides of the flow path and the spring force acts to compress the flow path and increase the flow resistance of the flow path between the two surfaces. Application of force to the actuation mechanism decreases the force applied to the segment of flow path between the two surfaces, decreasing the flow resistance of the valve.

In one embodiment, the injection device comprises a valve residing between the cannula and reservoir that is actuated magnetically. The valve is normally closed by the action of an internal spring or compression element to press a sealing element against a valve seat. The sealing element or the valve seat comprises a magnetic or paramagnetic material that may be moved or translated externally without physical connection to the internal valve elements. Movement of a magnet or activation of a magnetic field on the device external to the valve allows a flow path to be created between the sealing element and the valve seat to allow for delivery of the injection material. Progressive movement of the external magnet or magnetic field progressively opens the flow path in the valve to increase flow through the valve.

In the embodiments of the device with a sealing element and valve seat, the valve seat may be asymmetrical or have grooves to preferentially create a flow path in a predetermined region of the valve seat. In particular for delivery of suspensions of a drug or biological material, features of the sealing element and valve seat to preferentially open a region of the valve for flow creates a flow path with greater cross-sectional area to prevent clogging of the flow path by the suspension.

The cannula of the device is a tubular element of a small gauge size to limit trauma to the ocular tissues and allow for a self-sealing cannula puncture. The cannula may be sized from 20 gauge to 40 gauge, equivalent to an outer diameter of 0.90 mm to 0.08 mm. To minimize trauma to the target tissue and promote sealing of the injection site, the cannula may be sized from 27 gauge to 40 gauge, equivalent to an outer diameter of outer diameter of 0.41 mm to 0.08 mm. The cannula may transition in diameter from one diameter to a smaller diameter at the distal end. The cannula may be constructed from a metal, ceramic, high modulus polymer or glass. Suitable cannula materials include steel, nitinol, polyimide, polyamide, polyetheretherketone, polyethylene and polyethylene terephthalate. The length of the cannula for insertion in the target tissue or tissue space is selected to match the target location for the injection and taking into account the variation in target location due to anatomical variability. The cannula may have some additional length to allow manipulation of the distal tip in the tissue space or bleb during formation by the injection material. The length of the portion of the cannula intended for insertion into the tissue or tissue space may range from 1 mm to 20 mm. The cannula may be straight or have a curved configuration. The cannula may have a bevel to aid initial tissue penetration. The cannula may be colored to aid in visualization of the cannula once it is placed into the tissues or tissue spaces.

In one embodiment, the reservoir for the injection material comprises a cartridge that may be inserted in the body of the device prior to use. The cartridge comprises a tubular element with a lumen, a closed distal end and an open proximal end. A sliding fluid seal is sized to fit inside the lumen of the cartridge such that it may be moved within the tubular element. The closed distal end may incorporate a fixed fluid seal. The cartridge may be supplied with a removable outer tubular body and plunger in order to fill the cartridge from a vial containing the injection fluid. The proximal end of the tubular outer body comprises an inner cavity in order to receive the cartridge. The distal end of the inner cavity may incorporate a piercing element to pierce the distal seal of the cartridge when the cartridge is inserted into the tubular outer body. The piercing element is configured with a lumen to provide a flow path from the cartridge to the cannula of the device. The piercing element may be a needle which is beveled, a rigid segment of tubing or a rigid connector with a lumen. Alternatively, the cartridge may incorporate a needle, a rigid segment of tubing or a connector with a lumen that may pierce a septum on the distal end of the inner cavity of the tubular body to provide a flow path from the cartridge to the cannula. Placement of the cartridge in the inner cavity of the device configures the plunger of the device into position to move the proximal fluid seal distally to displace the injection material. In one embodiment, placement of the cartridge in the device also acts to pierce the distal seal with a needle, a segment of rigid tubing or a connector with a lumen to provide a flow path for the injection material in the cartridge to the cannula. In one embodiment, the proximal portion of the distal seal and the distal portion of the proximal seal are configured with complementary surfaces shaped to provide a low dead volume. In one embodiment, the proximal seal may be cone shaped with the distal seal having a conical depression on the proximal surface to mate to the proximal seal with no or minimal fluid entrapment between the mating surfaces. Placement of the cartridge into the body of the device may compress a spring to pressurize the injection material. Alternatively, the force mechanism to displace the plunger may be activated after insertion of the cartridge to pressurize the injection material.

In one embodiment the valve is opened and closed by an actuation mechanism located on the external surface of the body of the device. The actuation mechanism is located to allow holding and use of the device in a natural hand position to allow the distal tip to be advanced and positioned within tissue or a tissue space while activating and controlling delivery of the injection material. In one embodiment, the actuation mechanism comprises two or more mechanical elements on the body of the device configured to be activated by squeezing of the elements toward each other by the thumb and forefinger of the hand holding the device. In the case of two mechanical elements, the elements may be positioned on opposite sides of the device. In the case of greater than two mechanical elements, the elements may be positioned at equal spacing around the circumference of the device. The squeezing action provides stabilization of the device position to allow control of injection flow rate while holding the distal tip of the device in a desired tissue or tissue space location.

In one embodiment the source of force for the plunger is a spring or a pressurized gas reservoir providing a force in the range of 75 to 500 grams force. In one embodiment the source of force is a compressed force element with a near constant force element that is applied to the plunger to provide consistent flow characteristics. The near constant force element may comprise compressed struts that provide a plateau of spring force in the range of 15 to 200 grams force per mm of displacement. The struts may be fabricated from metals such as steel or nitinol, or polymers such as polyimide or polyamide. In one embodiment the struts are radially arranged along the axis of compression. In one embodiment the struts are linearly aligned across the axis of compression. The number of struts, width and length of the struts may be adjusted to provide the desired applied force.

In one embodiment, the source of force is coupled to a means to provide steady flow characteristics by damping the force applied to the piston. The damping may be coupled to a linear spring element to provide steady force characteristics or to a constant force element to further stabilize flow characteristics. The damping may comprise a source of friction that is matched to the source of force such as decreasing friction during displacement to reduce the force of a linear spring. The damping may comprise a viscous damping element such as a viscous fluid filled chamber that is displaced through a flow restricting orifice during progressive motion of the plunger.

In one embodiment, the device comprises a tissue interface on the distal tip of the cannula. The tissue interface is sized to fit to the outside diameter of the cannula and is slidably disposed on the cannula. The tissue interface remains on the surface of the tissue that is penetrated by the cannula and acts to seal the cannula puncture and protect the tissue at the puncture site from trauma while the injection material is entering the tissue and creating a space. In one embodiment, the tissue interface is elastically compressible to help create a seal on the tissue surface. The tissue interface may be configured to allow elastic reduction in length of the tissue interface during compression against the target tissue surface such as shaping the tissue interface as a bellows or mesh. In one embodiment a sealing force of the tissue interface is provided by a secondary force element such as a compression spring between the body of the device and the proximal end of the tissue interface. In one embodiment, the tissue interface is configured to allow an elastic reduction in length during cannula advancement to apply a sealing force.

In one embodiment, a friction element disposed in or about the tissue interface increases the force required to move the tissue interface proximally along the cannula, thereby promoting contact of the tissue interface with the surface of the eye and maintaining a seal against the tissue surface during cannula advancement. In one embodiment, the tissue interface is comprised of an axially compressible or deformable material which is fixed at the proximal end of the cannula and free at the distal end. Once in contact with the tissue surface, the tissue element compresses or deforms axially allowing the cannula to penetrate the tissues while maintaining a sealing force against the tissue surface. Once the tissue space is created by the pressure and flow of the injection material, the pressure within the tissue space decreases and the cannula may be removed. The tissue interface is constructed from a soft, deformable material such as a rubber or low modulus polymer to conform to the tissue surface. The tissue interface material may be clear or translucent to facilitate viewing of the cannula during initial insertion into the target tissue. The tissue interface may have planar external surfaces on each side of the cannula to facilitate viewing of the cannula tip when it is within the tissue interface.

In one embodiment, the tissue interface is attached to the body of the device by one or more collapsible elements. The collapsible element is configured to not allow an increase in length to prevent the tissue interface from being displaced from the tip of the cannula. The collapsible element allows a reduction in length, thereby allowing proximal travel of the tissue interface during advancement of the cannula into tissues. In one embodiment, the collapsible element comprises one or more elongated struts that may deform, bend or fold away from the cannula during proximal travel of the tissue interface. In one embodiment, the collapsible element comprises a section of tubing concentric to the cannula that has been cut to form openings along the axial length of the tubing to form collapsible struts. The shape and configuration of the collapsible struts may be tailored to provide a desired force-displacement characteristic of the tissue interface.

In one embodiment, the collapsible element provides a sealing force which transitions from an increasing spring-like force per unit displacement to a constant force independent of displacement to keep the tissue interface in sealing contact to the eye surface without undue application of force with further cannula advancement into the eye. The transition to a constant force is designed to occur after a length of the cannula tip is inserted into ocular tissue or tissue space, corresponding to a compression or collapse of the collapsible element of 0.3 mm to 2 mm. In one embodiment, the collapsible element provides for contact of the tissue interface to the surface of the eye during initial insertion of the cannula into the target tissue surface but collapses to provide little or no resistance to proximal movement of the tissue interface along the cannula after the tip of the cannula is fully inserted into tissue. The collapsible element may be assembled from components in a tube-like configuration or alternatively cut from a segment of tubing such as a laser machined nickel titanium alloy (Nitinol) or polyimide tube.

To use the injection device, the injection material is placed in the reservoir and the force element activated to pressurize the injection material. The distal tip of the device is placed against the target tissue and the distal tip of the cannula advanced into the tissue. The injection material is under pressure for injection prior to placement of the distal tip of the device into the target tissue, but the injection material cannot exit the device due to the closed flow regulating valve. Once inserted into tissue, the user activates the actuation mechanism gently to open the valve and create injection pressure at the tip of the cannula. Once a space for the injection material is reached, the injection material begins to flow through the cannula and into the tissue to form a space or bleb of fluid. The injection rate may be increased or decreased by the user while simultaneously positioning the distal tip of the cannula in the space being created to shape the formed tissue space or bleb to the desired location and geometry.

FIG. 1 depicts the device applied to an eye in order to perform an injection into the subretinal space. The device 1 is inserted into the eye 2 at the par plana 3. The distal end of the device 1 is advanced to the posterior surface of the eye and the distal tip inserted through the retina and the device 1 is actuated to inject sufficient injection material to create a subretinal space 4.

Figure 2:
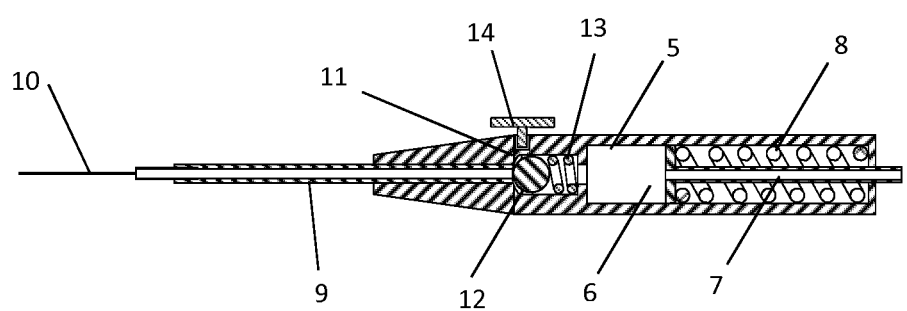
FIG. 2 depicts one embodiment of the device with an externally deformable valve.

In one embodiment of the device, as shown in the schematic of FIG. 2, the device is comprised of a body portion 5 which encloses a reservoir 6 and a valve mechanism. The proximal end of the body 5 contains a plunger 7 and a plunger spring 8 which acts as the force element to expel the injection material. The distal end of the body 5 is attached to a hollow shaft 9. The distal end of the hollow shaft 9 is attached to a hollow cannula 10. The central portion of the body 5 contains a valve mechanism which is comprised of a deformable valve seat 11, a spherical valve sealing element 12, a valve spring 13 and a valve actuator 14.

Figure 3A:
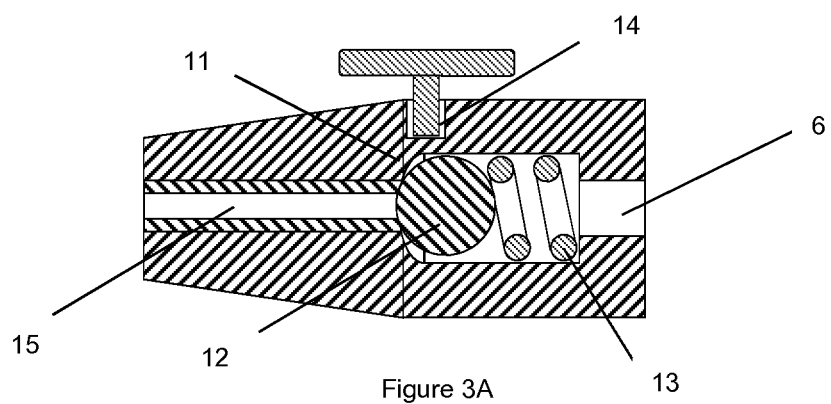
FIG. 3A depicts the valve of FIG. 2 in a closed position.
Figure 3B:
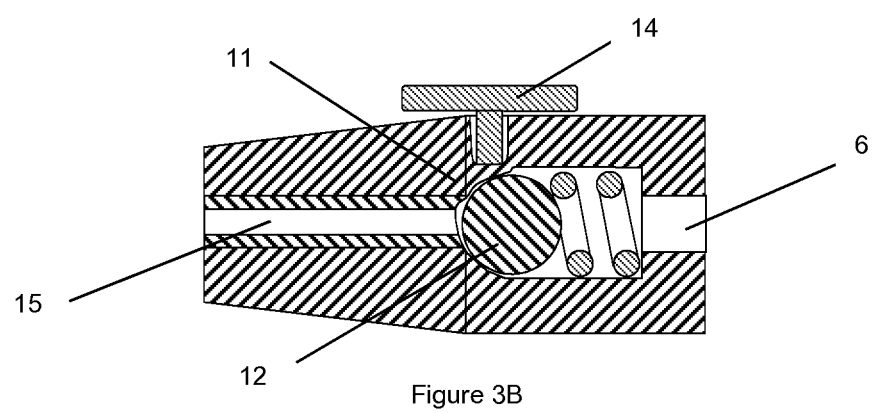
FIG. 3B depicts the valve of FIG. 2 in an open position.

A section view of the valve mechanism activation is shown in FIG. 3A and FIG. 3B. In FIG. 3A, the valve mechanism is shown in a closed position. The valve spring 13 provides a force on the valve sealing element 12 against the valve seat 11 thereby preventing flow from the reservoir 6 to the shaft lumen 15. The valve actuator 14 is in the undepressed position where it is in contact with the exterior of the valve seat 11, but not providing any force against the valve seat 11. In FIG. 3B, the valve actuator 14 is depressed resulting in deformation of the valve seat 11. The deformation of the valve seat 11 allows flow from the reservoir 6, around the valve sealing element 12 and into the shaft lumen 15.

Figure 4:
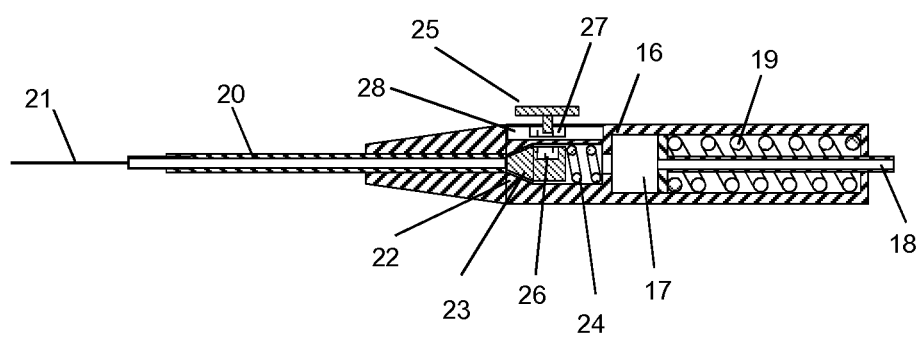
FIG. 4 depicts one embodiment of the device with a magnetically actuated valve.

In one embodiment of the device, as shown in the schematic of FIG. 4, the device is comprised of a body portion 16 which encloses a reservoir 17 and a valve mechanism. The proximal end of the body 16 contains a plunger 18 and a plunger spring 19 which acts as the force element to expel the injection material. The distal end of the body 16 is attached to a hollow shaft 20. The distal end of the hollow shaft 20 is attached to a hollow cannula 21. The central portion of the body 16 contains a valve mechanism which is comprised of a valve seat 22, a valve sealing element 23, a valve spring 24 and a valve actuator 25. The valve sealing element 23 contains a magnetic or paramagnetic element 26. The valve actuator contains a magnetic element 27 and is slidably disposed in a linear track 28.

Figure 5A:
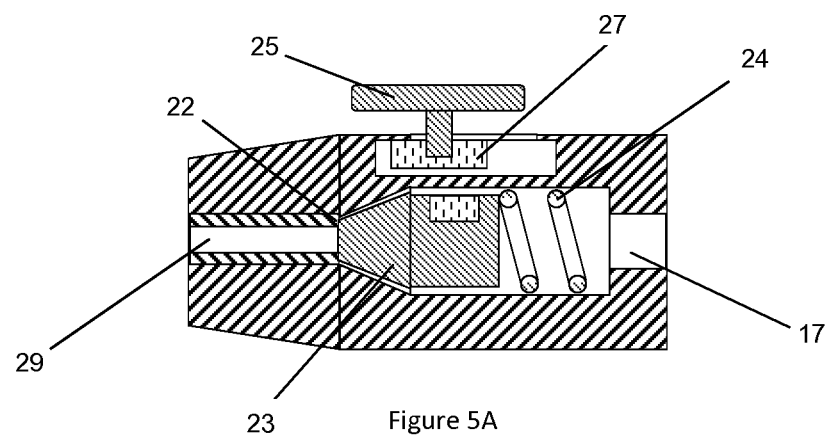
FIG. 5A depicts the valve of FIG. 4 in a closed position.
Figure 5B:
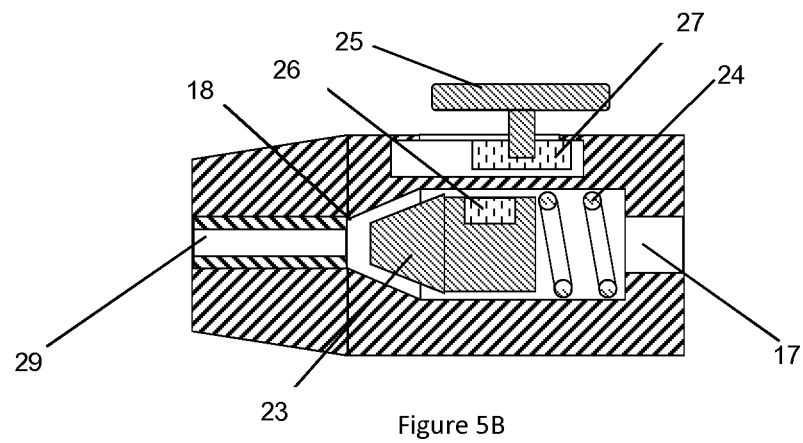
FIG. 5B depicts the valve of FIG. 4 in an open position.

A section view of the valve mechanism activation is shown in FIG. 5A and FIG. 5B. In FIG. 5A, the valve mechanism is shown in a closed position. The valve spring 24 provides a force on the valve sealing element 23 against the valve seat 22 thereby preventing flow from the reservoir 17 to the shaft lumen 29. The valve actuator 25 and actuator magnetic element 27 are in the distal position. In FIG. 5B, the valve actuator 25 is in the proximal position and the actuator magnetic element 27 provides a force to move the magnetic or paramagnetic element 26 and the valve sealing element 23 proximally against the valve spring 24, thereby opening a flow path that allows flow from the reservoir 17 to the shaft lumen 29.

Figure 6:
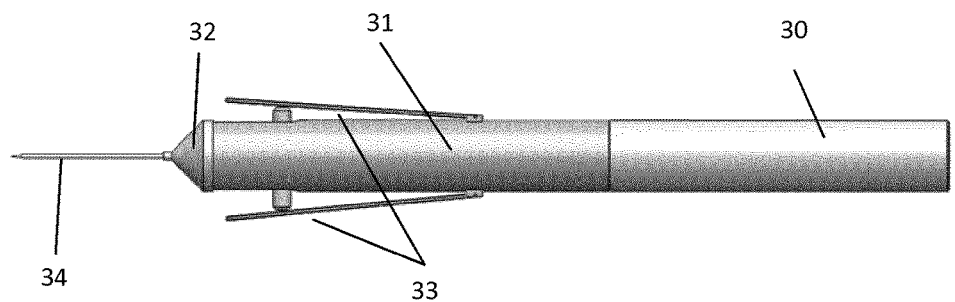
FIG. 6 depicts one embodiment of the device with a cartridge based fluid reservoir.
Figure 7:
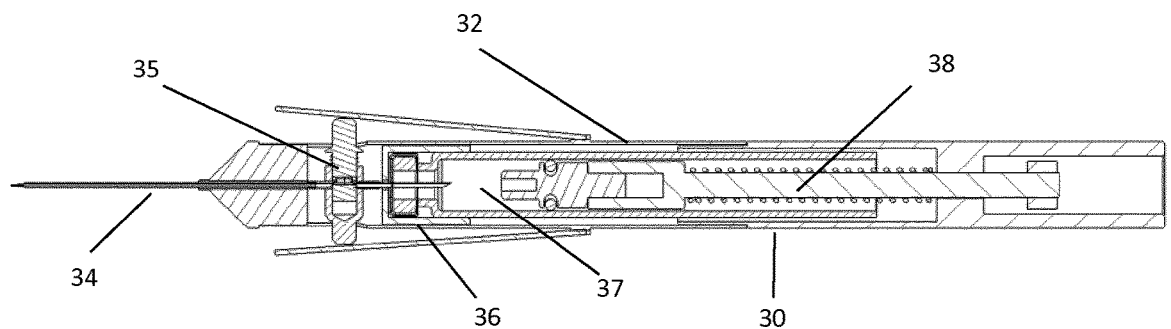
FIG. 7 depicts a section view of the device of FIG. 6.

A depiction of one embodiment of the device is shown in FIG. 6. The device comprises a proximal housing 30, a distal housing 31, a distal housing cap 32, two mechanical actuation levers 33 and a distal cannula assembly 34. FIG. 7 presents a section view of the device. Within the distal housing 32 resides valve assembly 35 attached distally to the distal cannula assembly 34 and proximally to a cartridge receiver assembly 36, and a cartridge assembly 37. Within the proximal housing 30 resides a plunger assembly 38.

Figure 8A:
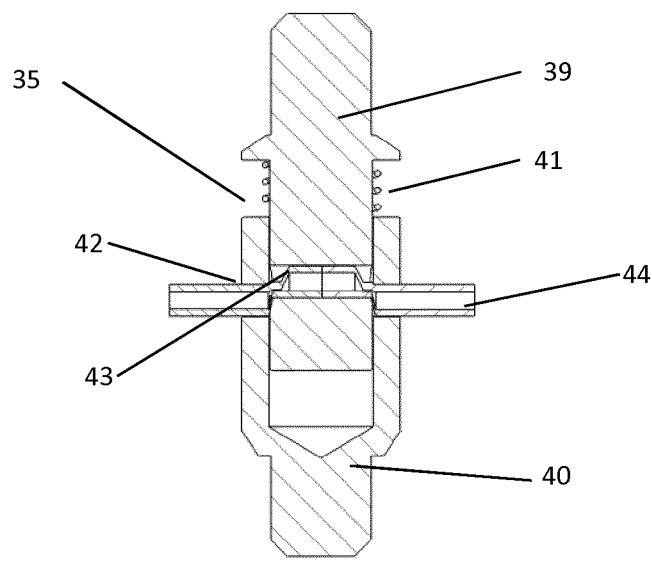
FIG. 8A depicts a section view of the valve of FIG. 6 in a closed position.
Figure 8B:
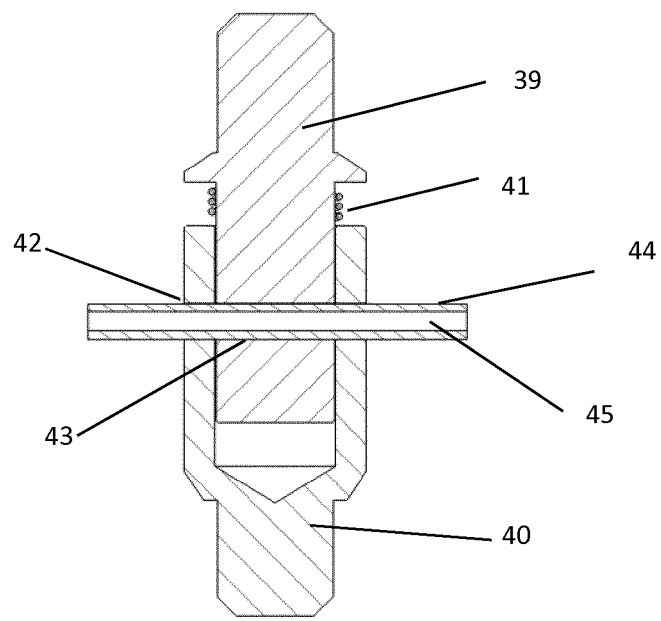
FIG. 8B depicts a section view of the valve of FIG. 6 in an open position.

A schematic of the valve mechanism of FIG. 7 is shown in FIGS. 8A and 8B. In FIG. 8A, the valve assembly 35 is in the normally closed position. The valve comprises an upper valve body 39, a lower valve body 40 and a valve spring 41. The valve bodies incorporate a through hole 42 and 43. An elastomer tube 44 is disposed through the valve holes 42 and 43. When the valve spring 41 presses on the lower valve body, the holes 42 and 43 are not axially aligned and the elastomer tube 44 is pinched closed. This represents the valve's normally closed position. As shown in FIG. 8B, when force is applied to compress the valve bodies 39 and 40 together against the valve spring 41, the valve holes 42 & 43 become aligned, thereby opening the lumen 45 of the elastomer tube 44 allowing fluid to flow through the valve.

Figure 9:
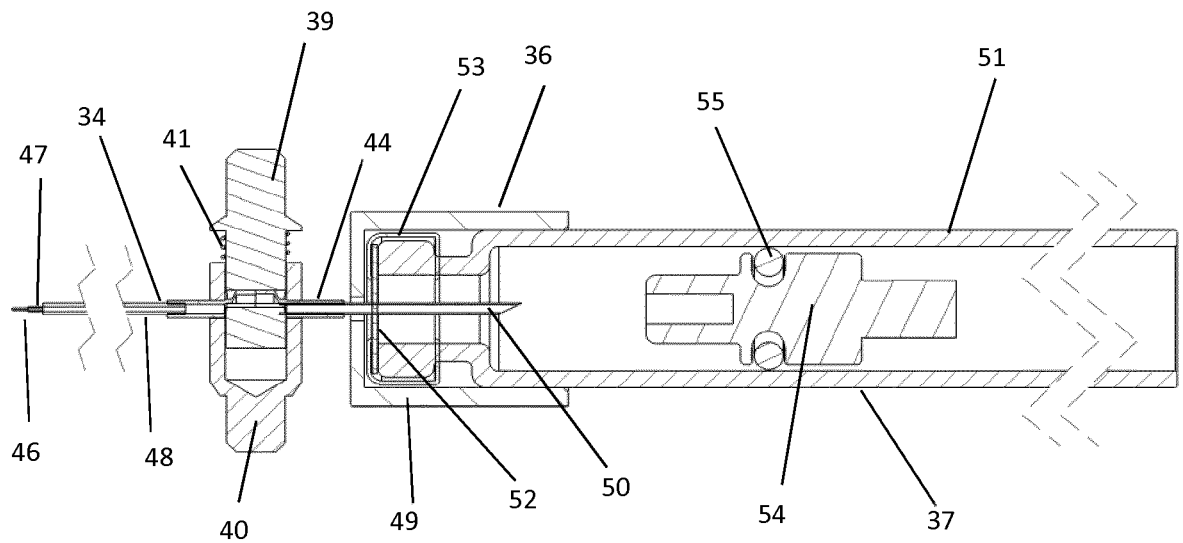
FIG. 9 depicts a section view of the internal fluid path components of FIG. 6.

FIG. 9 presents a schematic of the distal interior components of the device of FIG. 6. The distal cannula assembly 34 is comprised of a small diameter injection tube at the distal tip 46, bonded into a larger diameter mid shaft tube 47, which in turn is bonded into a larger diameter main shaft tube 48. The proximal end of the main shaft tube 48 is inserted into the distal end of the elastomer tube 44 of the valve assembly. The valve assembly comprises the upper valve body 39, the valve spring 41 and the lower valve body 40. The elastomer tube 44 is inserted through the valve bodies 39 and 40. A cartridge receiver 36 is comprised of a receiver body 49 and a receiver needle 50. The distal end of the receiver needle 50 is inserted into the proximal end of the elastomer tube 44 of the valve assembly. The proximal end of the receiver needle is beveled to pierce the septum 52 of the cartridge assembly. The cartridge assembly 37 is comprised of a cartridge body 51, a cartridge septum 52, a cartridge cap 53 and a moveable cartridge plunger 54. An o-ring 55 is mounted on the cartridge plunger to provide a sliding seal against the inner surface of the cartridge body 51.

Figure 10:
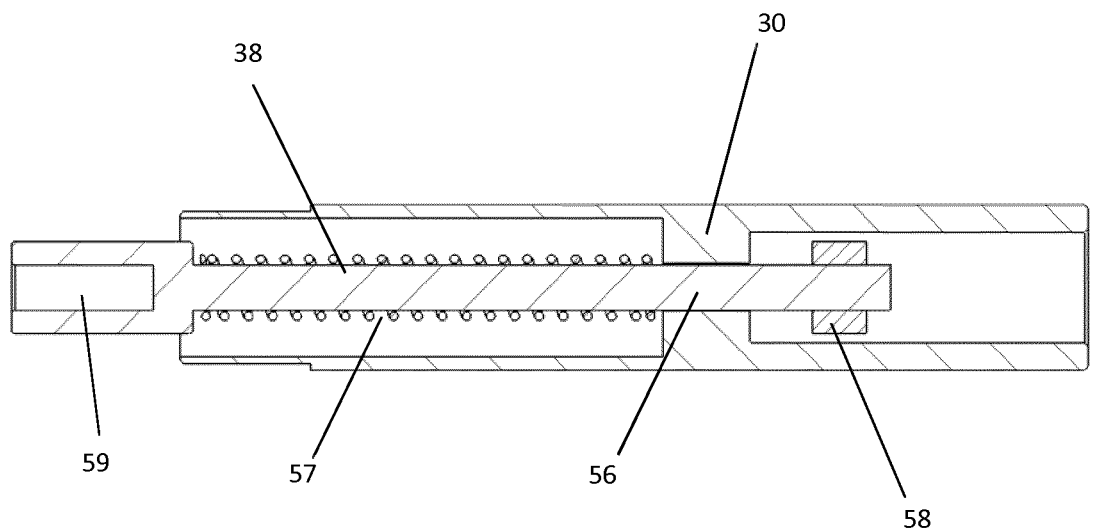
FIG. 10 depicts a section of the proximal components of FIG. 6.

FIG. 10 presents a schematic of the proximal components of the device of FIG. 6. A proximal housing 30 contains a plunger assembly 38. The plunger assembly 38 is comprised of a plunger shaft 56, a plunger spring 57 and a plunger stop 58. The distal end of the plunger shaft 56 incorporates a hole in the distal end to mate with the cartridge plunger.

Figure 11:
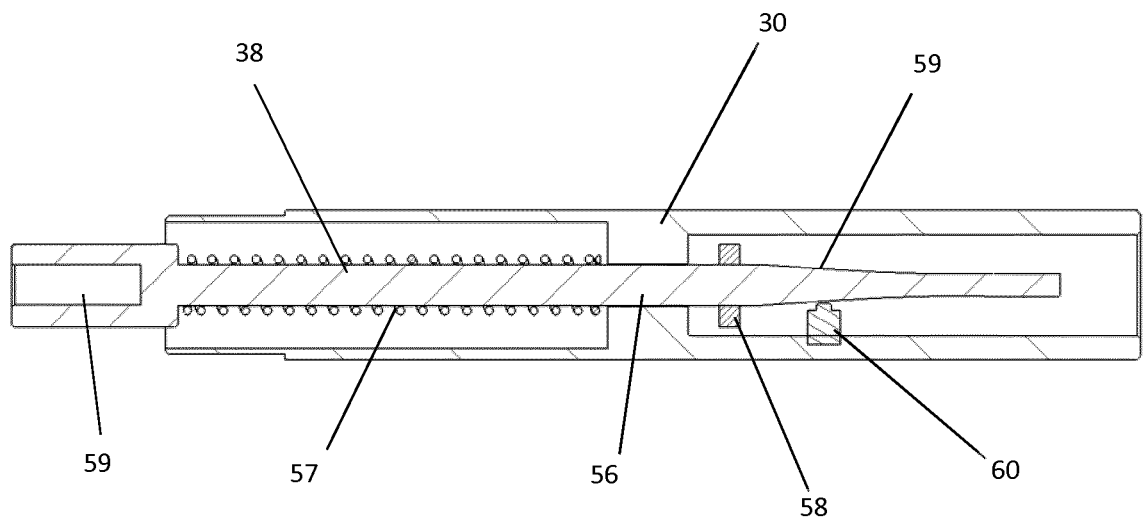
FIG. 11 depicts a section of an alternate embodiment of the proximal components of FIG. 6.

FIG. 11 presents a schematic of an alternate embodiment of the proximal components of the device of FIG. 6 incorporating a damping mechanism to control the speed of action. A proximal housing 30 contains a plunger assembly 38. The plunger assembly 38 is comprised of a plunger shaft 56, a plunger spring 57 and a plunger stop 58. The distal end of the plunger shaft 56 incorporates a hole in the distal end to mate with the cartridge plunger. The proximal end of the plunger shaft 56 incorporates a tapered segment 59. A frictional damping element 60 is disposed within the proximal housing 30 such that the tip of the damping element 60 is in varying contact with the tapered segment 59 of the plunger shaft 56.

Figure 12:
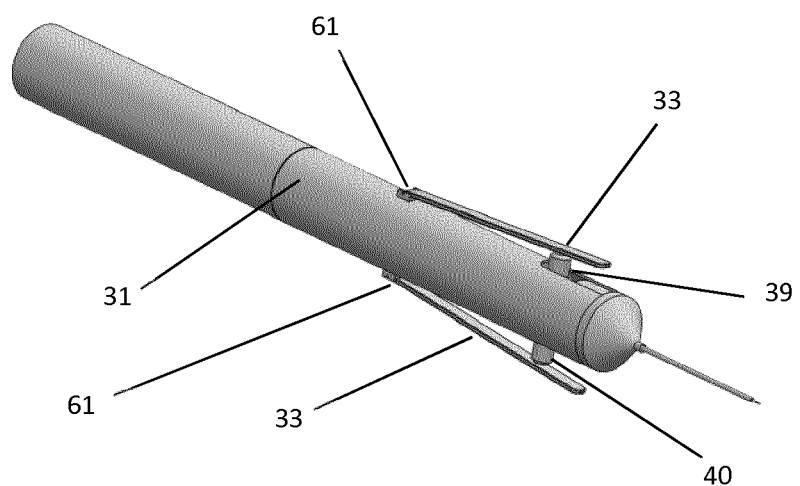
FIG. 12 depicts the actuation mechanism of FIG. 6.

FIG. 12 depicts the actuation mechanism of the device of FIG. 6. Two actuation levers 33 are proximally attached to the distal housing 31 by pivots 61. The distal ends of the levers 33 engage in the ends of the valve assembly bodies 39 and 40. When the levers 33 are manually depressed, the valve bodies 39 and 40 are forced together opening the valve as shown in FIG. 8B.

Figure 13:
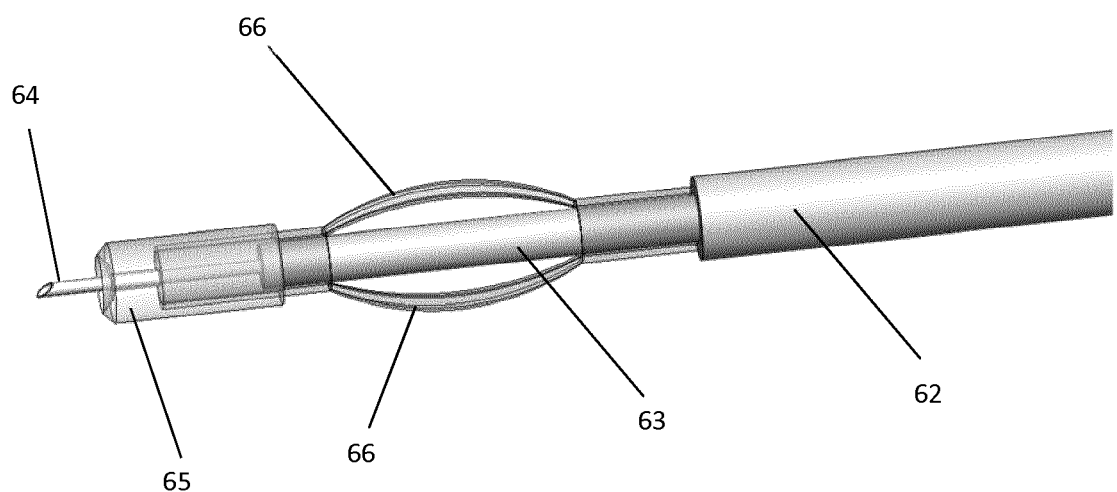
FIG. 13 depicts the distal end of a device with a tissue interface mechanism.

FIG. 13 depicts the distal end of one embodiment of the device which comprises a tissue interface mechanism. The distal end is comprised of a cannula assembly and a tissue interface assembly. The cannula assembly is comprised of a proximal main shaft 62 into which a small diameter mid shaft 63 is bonded. A fine gauge injection tube 64 is bonded into the end of the mid shaft 63. The tissue interface assembly is disposed about the mid shaft 63 and injection tube 64. The tissue interface is comprised of a distal elastomeric tissue seal 65 and a two axial compression elements 66. The tissue interface assembly is depicted in the activated position with the injection tube 64 penetrating the distal seal 65 and the compression elements 66 bent or deflected away from the longitudinal axis of the device.

A variety of therapeutic agents may be delivered by the present invention to the eye for the treatment of a variety of ocular diseases and conditions including inflammation, infection, macular degeneration, retinal degeneration, neovascularization, proliferative vitreoretinopathy, glaucoma, and edema. Useful drugs include, but are not limited to, steroids such as corticosteroids including dexamethasone, fluocinolone, loteprednol, difluprednate, fluorometholone, prednisolone, medrysone, triamcinolone, betamethasone and rimexolone; non-steroidal anti-inflammatory agents such as salicylic-, indole acetic-, aryl acetic-, aryl propionic- and enolic acid derivatives including bromfenac, diclofenac, flurbiprofen, ketorolac tromethamine and nepafenac; antibiotics including azithromycin, bacitracin, besifloxacin, ciprofloxacin, erythromycin, gatifloxacin, gentamicin, levofloxacin, moxifloxacin, ofloxacin, sulfacetamide and tobramycin; VEGF inhibitors such as tyrosine kinase inhibitors, antibodies to VEGF, antibody fragments to VEGF, VEGF binding fusion proteins; PDGF inhibitors, antibodies to PDGF, antibody fragments to PDGF, PDGF binding fusion proteins; anti-TNF alpha agents such as antibodies to TNF-alpha, antibody fragments to TNF-alpha and TNF binding fusion proteins including infliximab, etanercept, adalimumab, certolizumab and golimumab; mTOR inhibitors such as sirolimus, sirolimus analogues, Everolimus, Temsirolimus and mTOR kinase inhibitors; cells such as mesenchymal cells (e.g. mesenchymal stem cells), or cells transfected to produce a therapeutic compound; neuroprotective agents such as antioxidants, calcineurin inhibitors, NOS inhibitors, sigma-1 modulators, AMPA antagonists, calcium channel blockers and histone-deacetylases inhibitors; antihypertensive agents such as prostaglandin analogs, beta blockers, alpha agonists, and carbonic anhydrase inhibitors; aminosterols such as squalamine; antihistamines such as H1-receptor antagonists and histamine H2-receptor antagonists; therapeutic cells; tyrosine kinase inhibitors and nucleic acid based therapeutics such as gene vectors, plasmids and siRNA.

The invention will now be further described by way of reference to the following examples which are present for the purposes of illustration only and are not to be construed as being limitations to the claimed invention.

EXAMPLES

Example 1: Fabrication of One Embodiment of an Injection Device

The device according to one embodiment similar to the device shown in FIG. 2 was fabricated. A valve body 14.75 mm long was molded from silicone rubber of durometer 50 Shore A (Nusil, Part No. MED-4950) which comprises a proximal valve chamber of 3.43 mm diameter and 6.5 mm depth, dimensioned to accept a 3.175 mm diameter stainless steel spherical ball acting as a valve sealing element and a valve compression spring of 3.175 mm diameter and 8.26 mm long fabricated from 0.3 mm diameter wire. The valve body incorporated a valve seat of 1.91 mm diameter and 2.35 mm depth distal to the chamber, configured such that the ball acting as the valve sealing element was compressed against the valve seat by the valve spring. The molded valve body incorporated a compression flange 9.25 mm diameter and 1.25 mm thick on the proximal end. The distal end of the valve body was configured with a lumen to accept a 23 gauge tube that was press fit into the body.

A hollow tubular shaft was fabricated from 23 gauge hypodermic tubing with an inner diameter of 0.33 mm, an outer diameter of 0.64 mm and length 30 mm. A small segment of 30 gauge hypodermic tubing with an inner diameter of 0.15 mm and an outer diameter of 0.30 mm was adhesively bonded inside the distal tip of the 23 gauge tubing to act as a spacer between the 23 gauge shaft and the distal cannula. The 30 gauge shaft segment had an exposed length of 8.9 mm. A distal cannula was fabricated from a polyimide tube (Microlumen, Inc., Part No. 039-I) with an inner diameter of 0.09 mm and an outer diameter of 0.13 mm was adhesively bonded inside the 30 gauge shaft tubing with an exposed length of 6.35 mm. The distal shaft and cannula assembly was inserted into the distal end of the valve body and the valve sealing element and valve spring were assembled into the proximal end of the valve body thereby forming the valve assembly.

A reservoir was fabricated by cutting the distal end off of a 0.5 ml syringe body (Terumo, Model U-100) to a finished length of 40 mm. The finger grips of the syringe body were reduced in size to create a distal round flange portion 8.45 mm in diameter for mating to the valve body flange. The syringe body had an inner diameter of 3.63 mm and an outer diameter of 5.35 mm. The proximal end of the syringe body was tapped with an 8-32 UNC screw thread.

A plunger was fabricated from a stainless steel tube with an inner diameter of 0.9 mm and an outer diameter of 1.8 mm and a length of 72 mm. Two steel washers of 1.7 mm inner diameter and 3.25 mm outer diameter were press fit to the distal end of the plunger with a gap of 1.31 mm between the washers. A silicone O-ring of 1.07 mm inner diameter and 1.27 mm cross-section was mounted between the washers to act as a plunger seal inside the reservoir body. A plunger spring of 3.35 mm outer diameter, 38 mm in length and with a wire diameter of 0.3 mm was placed over the plunger shaft proximal to the washers. A plunger end cap was fabricated from a nylon 8-32 socket head cap screw. The screw axis was drilled to a diameter of 1.9 mm and the cap portion was machined to a diameter of 5 mm. The end cap was placed over the plunger proximal to the plunger spring. The proximal end of the plunger was attached to a Luer check valve (Qosina Inc., Part No. 80088) with a polyetheretherketone (PEEK) spacer machined to press fit into the check valve distal tube fitting and to receive the plunger shaft thereby forming a fluid tight connection between the check valve and the plunger. The assembled plunger was inserted into the reservoir and the end cap screwed into the proximal end of the reservoir thereby forming the reservoir assembly.

An actuation button was fabricated from PEEK. The button was comprised of a finger button portion and a shaft portion. The finger button portion was 9.7 mm diameter and 2.1 mm thick. The shaft portion was 8.8 mm long with a distal tip of 1.6 mm diameter. A device body was fabricated comprised of acrylonitrile butadiene styrene (ABS) in two portions. The distal portion was configured to receive the assembled valve body and the proximal portion was configured to receive the reservoir assembly. The two portions were configured to screw together to assemble. A hole was drilled in the distal portion perpendicular to the long axis of the device body to receive the shaft of the actuation button. The hole was located such that the shaft of the actuation button would contact the valve body at the proximal edge of the valve seat. Compression of the actuation button would cause compression of the valve body and deformation of the valve seat.

A central washer was fabricated from polytetrafluoroethylene (PTFE) with an inner diameter of 2.36 mm, an outer diameter of 8.95 mm and a thickness of 0.88 mm. The washer served to provide sealing between the valve flange and the reservoir flange and to compress the valve spring providing the sealing force of the valve sealing element against the valve seat. The valve assembly was inserted into the distal portion of the device body, the reservoir assembly was inserted into the proximal portion of the valve body and the central washer was inserted into the proximal portion to reside between the reservoir flange and the valve flange. The two portions of the device body were screwed together. The actuation button was inserted into the distal portion hole, completing the device assembly.

Example 2: Testing of Injection Device

A device according to Example 1 was fabricated. De-ionized water as the injection material was drawn up into a 1 ml syringe and the syringe was attached to the Luer fitting of the plunger check valve. Approximately 0.3 ml of water was filled into the reservoir causing the plunger to retract proximally and compressing the plunger spring thereby providing a force on the injection material in the device reservoir. No injection material flowed out of the distal cannula. The actuation button was depressed and water was seen flowing out of the distal cannula. The actuation button was released and the fluid flow stopped. The action was repeated with the same results.

Example 3: Testing of Injection Device in an Eye

A device according to Example 1 was fabricated. A porcine cadaver eye was prepared for using the device for a subretinal injection. The procedure was performed under a stereo microscope for ease of visualization. In order to access the retina in the cadaver eye, the cornea was completely removed at the limbus. The natural lens was carefully excised by cutting the zonular fibers away from the lens then lifting the lens out of the globe. The vitreous was removed en-masse leaving the retina behind. The device was loaded with 0.2 ml of 0.1% fluorescein solution using a 1 ml syringe filled with the fluorescein solution attached to the plunger check valve. The distal cannula was carefully inserted through the retina tissues and was advanced. The cannula deflected across the choroidal surface, traversing a short distance parallel to the tissues.

The actuation button was depressed for approximately 1.5 seconds during which time fluorescein solution could be seen creating and filling a space under the retina. After the injection time, the actuation button was released and flow from the cannula stopped and the cannula was withdrawn.

Example 4: Fabrication of One Embodiment of the Injection Device

The device according to one embodiment similar to the device shown in FIGS. 6 and 7 was fabricated. The device comprised a two-piece cylindrical housing and a housing cap holding a distal cannula assembly. The distal housing piece comprised an inner cavity in the proximal end sized to receive a cartridge containing the material for injection. Within the distal housing resided an assembly consisting of a receiver body for the cartridge and a valve body. On the outside of the distal housing, two mechanical actuation levers were placed 180 degrees apart to actuate the valve. The distal housing was fabricated from brass tubing 9.4 mm outer diameter and 8.7 mm inner diameter and 56.5 mm long. The proximal housing piece comprised an open proximal end sized to fit over the fluid filled cartridge and a spring loaded plunger assembly sized to fit into a sliding seal within the cartridge to provide force to expel the contents of the cartridge. The proximal housing piece was fabricated from brass tubing 10.3 mm outer diameter and 9.5 mm inner diameter and 62 mm long, sized to slidably mate with the distal housing piece.

A receiver and valve assembly were fabricated to fit within the distal housing body. The receiver was fabricated from polyethylene and had a closed distal end and an open proximal end. The open proximal end was sized to accommodate the distal end of the cartridge with a slight interference fit. A hole was drilled in the axis of the receiver and a short segment of 23 gauge hypodermic tubing was press fit into the receiver. The hypodermic tubing extended proximally within the receiver and the proximal end of the tube was beveled to allow it to pierce the distal seal of the cartridge when the cartridge was inserted into the housing.

A two-piece valve body was fabricated from acetal polymer. The first piece of the valve body comprised a cylindrical boss on one end that was sized to fit within a receiver hole in the second piece. A stainless steel compression spring was wound to fit around the cylindrical boss on the first piece to provide force against the second piece. A hole was drilled through both pieces at 90 degrees to the axis of the pieces, such that when the spring was compressed sliding the boss into the receiver, the holes were aligned in a coaxial manner and therefore open and when the spring forced the two pieces apart, the hole axes were no longer aligned and the valve was closed. A piece of silicone elastomer tubing 0.30 mm inner diameter and 0.64 mm outer diameter was inserted through the hole. In the uncompressed state, the closed through hole pinched closed the silicone tube. In this manner, a normally closed valve was fashioned. When the valve pieces were compressed together, the opening of the hole would relieve the pinching of the silicone tubing allowing flow through the valve. The amount of flow could be controlled by the amount of compression of the two valve pieces. The distal end of the hypodermic tube of the receiver was bonded to the proximal end of the silicone valve tube. The outer ends of the valve body pieces were comprised of solid cylindrical bosses. The mechanical actuation levers were configured to press on the cylindrical bosses to actuate the valve mechanism.

The distal cannula assembly consisted of a length of 23 gauge hypodermic tubing press fit into the housing cap. The 23 gauge tubing extended distally from the cap for a length of 24 mm and proximally from the cap for 3 mm. A piece of 30 gauge hypodermic tubing was bonded into the distal ID of the 23 gauge hypodermic tubing and extended 4 mm beyond the end of the 23 gauge tubing. A piece of polyimide tubing 0.01 mm inner diameter by 0.13 mm outer diameter was bonded into the distal end of the 30 gauge tubing and extended 5 mm distally from the end. The proximal end of the 23 gauge tubing was bonded to the distal end of the silicone valve tube. The assembly comprising the distal cannula and housing cap, valve body and receiver body was inserted into the distal housing. Two mechanical actuation levers were machined from a single body of brass tubing 10.3 mm outer diameter and 9.5 mm inner diameter and 35 mm long wherein the proximal end of the tubing remained circular to allow mounting on the distal housing. Two wide slots were cut from the distal end of the tube along most of the tube length leaving two axial lengths of brass to serve as the lever arms. The lever body was slid over the distal housing and bonded into place such that the two lever arms were positioned over the valve body cylindrical bosses.

The proximal housing contained a plunger shaft and spring assembly. The plunger shaft was fabricated from polyetheretherketone (PEEK) and contained a hole at the distal end and reduced diameter shaft at the proximal end. The proximal 10 mm of the plunger shaft was threaded. The plunger distal end was sized to fit within the lumen of the fluid filled cartridge with the hole fitting over the proximal end of the cartridge sliding seal to allow force from the spring to be transferred to the sliding seal. A stainless steel compression spring was slid over the proximal end of the plunger. A spring stop was mounted inside the proximal device housing. The spring stop incorporated a hole allowing a sliding fit for the proximal end of the plunger shaft. The plunger shaft was placed through the spring stop and a nylon nut was threaded onto the proximal end of the shaft. In this manner the plunger shaft could be pushed proximally, compressing the spring to provide for the force to expel the contents of the cartridge.

A reservoir fluid cartridge assembly was fabricated. The cartridge body consisted of a standard glass 1.8 ml pharmaceutical grade cartridge with an 8 mm crown diameter. A distal seal was fabricated from silicone elastomer with a durometer of 10 Shore A. The seal was punched from a sheet using an 8 mm circular punch. The seal was placed on the crown and a standard 8 mm aluminum seal was placed over the end and crimped using a crimping tool. A sliding seal body was fabricated from PEEK. The distal end of the seal was machined to approximate the inner curvature of the glass cartridge so as to limit dead volume. A groove was circumferentially cut into the body and a silicone o-ring assembled on to it to provide a sealing force between the body and the glass cartridge. The proximal end of the body comprised a threaded boss 5 mm long. A removable manual plunger was fabricated from a standard polypropylene syringe plunger. The distal tip of the plunger was cut-off and the distal end was threaded so as to be able to be attached to the sliding seal body in the cartridge. A filling syringe was fabricated from a standard 3 ml polypropylene Luer lock syringe barrel and a needle assembly. The needle assembly comprised a 25 gauge hypodermic needle inserted into a Luer hub fitting such that the proximal end of the needle extended proximally from the Luer hub 9.5 mm. The proximal end of the needle was beveled to allow it to pierce the distal seal of the cartridge. The needle assembly was mounted to the syringe barrel.

In use, the cartridge was inserted into the syringe barrel and the plunger was attached to the cartridge sliding seal. The needle was inserted into a fluid filled vial and the plunger and seal pulled proximally, withdrawing fluid into the cartridge. The syringe body and plunger were removed from the cartridge. The cartridge was inserted into the distal device housing until seated in the receiver. The proximal device housing was assembled to the distal housing, engaging the distal end of the plunger shaft with the cartridge sliding seal and compressing the plunger spring with the plunger shaft. As the valve was closed, no fluid could flow. Manual pressure on the actuating levers compressed the valve body pieces together, opening the silicone tubing and allowing flow through the device and out through the distal polyimide tube. Increasing pressure on the actuators increased the lumen opening of the silicone tube thereby increasing flow through the device.

The invention claimed is:

1. An injection device comprising:
    an elongated body with a hollow cannula secured to a distal end of the body;
    a reservoir for an injection material to be delivered through the cannula;
    a plunger with a force element that provides an injection force to the injection material contained in the reservoir;
    a valve disposed in a flow path between the reservoir and the cannula wherein the valve is normally closed with the injection force applied to the injection material; and
    a valve actuation mechanism for the valve that is external to the valve, wherein the valve actuation mechanism is attached to the elongated body and a portion of the actuation mechanism to be activated by the user is located on an external surface of the device;
    wherein actuation of the valve actuation mechanism opens a flow path through the valve, and wherein progressive actuation of the valve actuation increases a flow rate of injection.

2. The injection device of claim 1 wherein the valve comprises:
    a flow path comprising an elastically deformable material or combination of elastically deformable materials;
    a mechanism external to the flow path that applies a compression force to close the flow path in the valve;
    wherein relieving of the compression force by the valve actuation mechanism allows the elastic return of the flow path from a closed or partially closed configuration to a configuration with a decreased flow resistance.

3. The injection device of claim 2 wherein the elastically deformable material or combination of materials comprises an elastomeric tube.

4. The injection device of claim 2 wherein the mechanism comprises two opposing surfaces coupled to a spring force acting to reduce the distance between the two opposing surfaces wherein the two opposing surfaces are configured on opposite sides of the flow path to compress and increase the flow resistance of the flow path.

5. The injection device of claim 1 wherein the valve comprises:
    an internal valve spring;
    a sealing element; and
    a valve seat;
    wherein the sealing element is pressed against the valve seat under a sealing force by the valve spring, and an external force against the valve by the valve actuation mechanism deforms the valve seat to create a flow path.

6. The injection device of claim 1 wherein the valve comprises:
    an internal valve spring;
    a sealing element; and
    a valve seat;
    wherein the sealing element is pressed against the valve seat under a sealing force by the valve spring, and at least one of the sealing element and the valve seat are magnetic or paramagnetic, wherein the actuation mechanism comprises a magnet which when translated opens a flow path between the sealing element and the valve seat.

7. The injection device of claim 1 additionally comprising a connector, valve or septum to fill the reservoir.

8. The injection device of claim 1 wherein the cannula has an outer diameter between 0.41 mm to 0.08 mm.

9. The injection device of claim 1 wherein the reservoir comprises a cartridge that is inserted into the device prior to use.

10. The injection device of claim 1 wherein the actuation mechanism comprises two opposing mechanical elements on opposite sides of the body of the device configured to be activated by squeezing the elements toward each other.

11. The injection device of claim 1 wherein the force element is coupled to a damping mechanism.

12. The injection device of claim 1 additionally comprising a tissue interface secured to the distal end of the cannula, wherein the tissue interface comprises a distal elastomeric seal, and wherein the tissue interface is sized to fit to the outside diameter of the cannula and is slidably disposed on the cannula.

13. The injection device of claim 12 wherein the tissue interface is elastically compressible in length.

14. The injection device of claim 12 additionally comprising a secondary force element between the body of the device and the tissue interface.

15. The injection device of claim 12 additionally comprising a collapsible element between the body of the device and the tissue interface.

16. The injection device of claim 5 wherein the valve comprises grooves or an asymmetric configuration to create a flow path in a preferential region of the valve seat.

17. A method for treatment of an ocular disease or condition comprising:
    activating the device of claim 1 to provide an injection force on the injection material;

placing the distal tip of the cannula of the device into the subretinal space of an eye; and activating the actuation mechanism to deliver the injection material to the subretinal space.

18. A method for treatment of an ocular disease or condition comprising:

activating the device of claim 1 to provide an injection force on the injection material;

placing the distal of the cannula of the device into the subconjunctival space of an eye; and activating the actuation mechanism to deliver the injection material to the subconjunctival space.

19. A method for treatment of an ocular disease or condition comprising:

activating the device of claim 1 to provide an injection force on the injection material;

placing the distal of the cannula of the device into the suprachoroidal space of an eye; and activating the actuation mechanism to deliver the injection material to the suprachoroidal space.

20. A method for treatment of an ocular disease or condition comprising:

activating the device of claim 1 to provide an injection force on the injection material;

placing the distal of the cannula of the device into the subtenon space of an eye; and activating the actuation mechanism to deliver the injection material to the subtenon space.

21. A method for the injection of a material into the subretinal space comprising:

activating the device of claim 1 to provide an injection force on the injection material;

placing the distal tip of the cannula of the device into the subretinal space of an eye; and activating the actuation mechanism to deliver the injection material to the subretinal space.

22. A method for the injection of a material into the subconjunctival space comprising:

activating the device of claim 1 to provide an injection force on the injection material;

placing the distal tip of the cannula of the device into the subconjunctival space of an eye; and activating the actuation mechanism to deliver the injection material to the subconjunctival space.

23. A method for the injection of a material into the suprachoroidal space comprising:

activating the device of claim 1 to provide an injection force on the injection material;

placing the distal tip of the cannula of the device into the subconjunctival space of an eye; and activating the actuation mechanism to deliver the injection material to the suprachoroidal space.

24. A method for the injection of a material into the subtenon space comprising:

activating the device of claim 1 to provide an injection force on the injection material;

placing the distal tip of the cannula of the device into the subconjunctival space of an eye; and activating the actuation mechanism to deliver the injection material to the subtenon space.

25. The method of claim 17 wherein the injection material composition comprises a steroid, a non-steroidal anti-inflammatory agent, an antihistamine, an aminosterol, an antibiotic, a VEGF inhibitor, an anti-TNF alpha agent, a mTOR inhibitor, a cell, a neuroprotective agent, a kinase inhibitor or a nucleic acid.

26. The method of claim 17 wherein the ocular disease or condition is inflammation, infection, macular degeneration, retinal degeneration, neovascularization, proliferative vitreoretinopathy, glaucoma, or edema.

* * * * *